United States Patent [19]
Johnston et al.

[11] 3,948,910
[45] Apr. 6, 1976

[54] AMINOHALOPYRIDINE-N-OXIDES

[75] Inventors: Howard Johnston; Alin H. Gulbenk, both of Walnut Creek, Calif.

[73] Assignee: The Dow Chemical Company, Midland, Mich.

[22] Filed: Dec. 28, 1973

[21] Appl. No.: 429,301

[52] U.S. Cl. ........ 260/247.5 G; 71/94; 260/293.69; 260/296 R
[51] Int. Cl.² ........................................ C07D 295/08
[58] Field of Search..... 260/247.5 G, 293.69, 296 R

[56] References Cited
UNITED STATES PATENTS

| | | | |
|---|---|---|---|
| 3,495,969 | 2/1970 | Driscoll............................ | 260/247.5 |
| 3,555,031 | 1/1971 | Long et al....................... | 260/296 R |
| 3,634,439 | 1/1972 | Ayad............................... | 260/296 R |

OTHER PUBLICATIONS
Mizukami et al., Shionogi Kenkyusho Nempo 16, 29–36 (1966), C.A., Vol. 66;10.827.

*Primary Examiner*—Lorraine A. Weinberger
*Assistant Examiner*—Paul J. Killos
*Attorney, Agent, or Firm*—S. Preston Jones

[57] ABSTRACT

Compounds are prepared which correspond to the formula

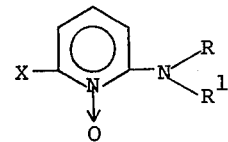

wherein X represents chloro or bromo; R represents hydrogen; R¹ represents a straight or branched chain alkyl of 3 to 6 carbon atoms or cyclohexyl or R and R¹ taken together with the nitrogen atom represent morpholino, pyrrolidinyl, piperidino, 2-(loweralkyl)piperidino (wherein alkyl represents from 1 to 4 carbon atoms), hexamethylenimino or tetrahydro-1-pyridyl.

14 Claims, No Drawings

3,948,910

AMINOHALOPYRIDINE-N-OXIDES

PRIOR ART

Various aminohalopyridines and various pyridine-N-oxides are known in the prior art. Katritzky, J. Chem. Soc. Part 1, 191–195 (1957) teaches the preparation of aminopyridine-1-oxides. Roberts et al., Chem. Communications 1967 (17) 893–894 (Chem. Abstracts 67 107876w (1967) teach the preparation of tetrachloroaminopyridine-1-oxides. U.S. Pat. No. 3,535,328 and German Pat. No. 2,007,100 are directed to various pyridine compounds. British Pat. No. 1,311,589 is directed to various halopyridine-1-oxides.

SUMMARY OF THE INVENTION

The present invention is directed to compounds corresponding to the formula

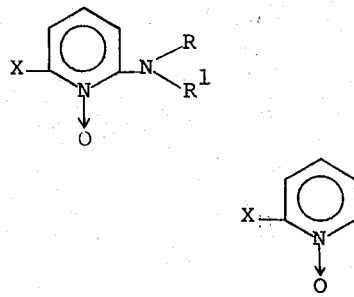

wherein X represents chloro or bromo; R represents hydrogen; $R^1$ represents a branched chain alkyl of 3 to 6 carbon atoms or R and $R^1$ taken together with the nitrogen atom represents 1-morpholino, 1-pyrrolidinyl, 1-piperidino, 1-(2-(loweralkyl)-piperidino) (wherein alkyl represents from 1 to 4 carbon atoms), 1-hexamethylenimino or tetrahydro-1-pyridyl.

The pyridine-N-oxides of the present invention are crystalline solids or oils which are of low solubility in water and of moderate solubility in many common organic solvents; they are highly active as both pre- and post-emergent herbicides useful in the kill and control of both broad and narrow-leaf plants.

Representative pyridine-N-oxides of the present invention include:

6-Chloro-2-(n-propylamino)pyridine-N-oxide;
6-Bromo-2-(n-propylamino)pyridine-N-oxide;
6-Chloro-2-(isopropylamino)pyridine-N-oxide;
6-Bromo-2-(isopropylamino)pyridine-N-oxide;
6-Chloro-2-(n-butylamino)pyridine-N-oxide;
6-Bromo-2-(n-butylamino)pyridine-N-oxide;
6-Chloro-2-(isobutylamino)pyridine-N-oxide;
6-Bromo-2-(n-pentylamino)pyridine-N-oxide;
6-Chloro-2-(isopentylamino)pyridine-N-oxide;
6-Chloro-2-(1,3-dimethylbutyl)amino)pyridine-N-oxide;
6-Bromo-2((1,3-dimethylpropyl)amino)pyridine-N-oxide;
6-chloro-2-(cyclohexylamino)pyridine-N-oxide;
6-Chloro-2-(1-piperidino)pyridine-N-oxide;
6-Bromo-2-(1-piperidino)pyridine-N-oxide;
6-Chloro-2-(1-(2-methylpiperidino))pyridine-N-oxide;
6-Chloro-2-(1-(2-ethylpiperidino))pyridine-N-oxide;
6-Bromo-2-(1-(2-n-butylpiperidino)pyridine-N-oxide;
6-Chloro-2-(4-morpholino)pyridine-N-oxide;
6-Bromo-2-(4-morpholino)pyridine-N-oxide;
6-Chloro-2-(1-pyrrolidinyl)pyridine-N-oxide;
6-Chloro-2-(1Hexamethylenimino)pyridine-N-oxide
6-Chloro-2-(tetrahydro-1pyridyl)pyridine-N-oxide and
6-Bromo-2-(tetrahydro-1-pyridyl)pyridine-N-oxide.

The new compounds of the present invention can be prepared by reacting a 2,6-dichloro- or dibromopyridine-N-oxide with an excess of an appropriate amine reactant corresponding to the formula

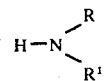

wherein R and $R^1$ are as hereinbefore defined.

The reaction is carried out in the presence of an inert organic solvent and the excess amine reactant acts as an acid receiver for the hydrogen chloride or bromide formed during the reaction. This reaction can be presented as follows:

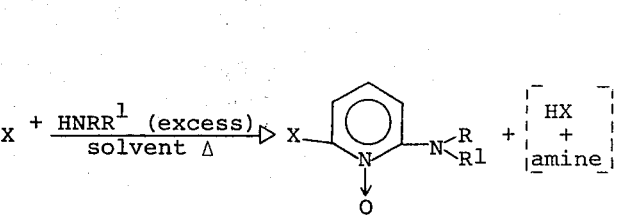

wherein X represents chloro or bromo and R and $R^1$ are as hereinbefore defined.

The reaction is initiated by slowly adding an excess of the appropriate amine reactant to a mixture of the 2,6-dichloro- or dibromopyridine-N-oxide in the inert organic solvent. The mixture is thereafter heated with the reaction being carried out at a temperature of from about 50° to about 150°C. when employing an alkyl or cycloalkyl amine reactant (straight or branched chain alkyl amine or cyclohexylamine); and under reflux temperature conditions when employing a heterocyclic amine reactant (piperidine, pyrrolidine, morpholine, tetrahydro-1-pyridine or hexamethylenimine). The reaction is carried out for a period of from about ½ hour to about 5 hours. At the completion of the reaction, the reaction mixture is distilled to remove all or most of the solvent and the crude product removed by filtration either after quenching the reaction mixture to precipitate the product or by extraction of the reaction residue with a solvent such as benzene or hexane. The product, if desired, can be further purified by recrystallization from a solvent such as pentane, benzene, hexane or mixtures thereof.

Representative inert organic solvents which can be employed in carrying out the reaction include for example, dimethylsulfoxide, dimethylformamide, ethyleneglycol or dimethylether when employing an alkyl or cycloalkyl amine reactant and benzene, toluene or chloroform when employing a heterocyclic amine reactant.

DESCRIPTION OF SOME PREFERRED EMBODIMENTS

The following examples illustrate the present invention and the manner by which it can be practiced but, as such, should not be construed as limitations upon the overall scope of the same.

Example I:
6-Chloro-2-(isopropylamino)pyridine-N-oxide

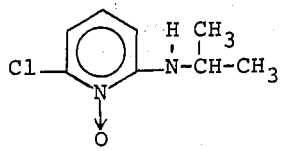

To a solution consisting of 10 grams (0.06 mole) of 2,6-dichloropyridine-N-oxide in 50 milliliters of dimethylsulfoxide was slowly added 7.9 grams (0.134 mole) of isopropylamine. The temperature of the mixture was 90°C. at the start of the reaction and was allowed to increase to 120°C. After a total reaction time of ~50 minutes, ¾ of the dimethylsulfoxide was removed by evaporation and the reaction mixture poured over ice. The solid precipitate which formed was removed by filtration and taken up in 500 milliliters of hot hexane. The 6-chloro-2-(isopropylamino)-pyridine-N-oxide product melting at 150°–151°C. and was recovered by filtration in a yield of 5 grams. Upon analysis, the product was found to have carbon, hydrogen, chlorine and nitrogen contents of 51.47, 5.96, 19.01 and 15.01 percent, respectively, as compared with the theoretical contents of 51.46, 5.94, 18.99 and 14.99 percent, respectively, calculated for the above named compound.

Example II:
6-Chloro-2-(n-butylamino)pyridine-N-oxide

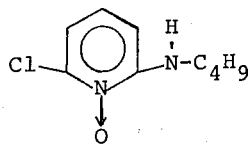

To a solution consisting of 9.9 grams (0.055 mole) of 2,6-dichloropyridine-N-oxide in 50 milliliters of dimethylsulfoxide was slowly added 8.4 grams (0.115 mole) of n-butylamine. The temperature of the mixture was 75°C. at the start of the reaction and was allowed to increase to 120°C. After a total reaction time of ~2½ hours, ¾ of the dimethyl sulfoxide was removed by evaporation and the reaction mixture poured into cold water. The solid 6-chloro-2-(n-butylamino)pyridine-N-oxide product which precipitated was recovered by filtration in the yield of 6.0 grams. The product melted was 103°–104°C. and was found upon analysis to have carbon, hydrogen, chlorine and contents of 54.1, 6.9, 17.9 and 13.8 percent, respectively, as compared with the theoretical contents of 54.0, 6.5, 17.8 and 14.0 percent, respectively, calculated for the above named compound.

Following the above teaching and reacting the appropriate amine with the appropriate dichloro- or dibromopyridine-N-oxide, the following compounds are prepared.

6-Chloro-2-(n-propylamino)pyridine-N-oxide having a molecular weight of 186.54;

6-Bromo-2-(n-propylamino)pyridine-N-oxide having a molecular weight of 231.08;

6-Chloro-2-(n-butylamino)pyridine-N-oxide, having a molecular weight of 200.64;

6-Bromo-2-(n-butylamino)pyridine-N-oxide, having a molecular weight of 245.10;

6-Chloro-2-(isobutylamino)pyridine-N-oxide, melting at 76°–78°C.

6-Bromo-2-(isobutylamino)pyridine-N-oxide, melting at 59°–62°C.

6-Bromo-2-(n-pentylamino)pyridine-N-oxide having a molecular weight of 258.12;

6-Chloro-2-((1,3-dimethylbutyl)amino)pyridine-N-oxide, melting at 101°–102°C.; and 6-Chloro-2-(cyclohexylamino)pyridine-N-oxide, melting at 155°–158°C.

Example III: 6-Chloro-2-(piperidino)pyridine-N-oxide

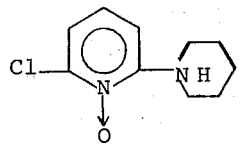

A solution was prepared by dissolving 10 grams (0.061 mole) of 2,6-dichloropyridine-N-oxide in 100 milliliters of benzene at 35 C. To this solution was added dropwise 10.3 grams (0.122 mole) of piperidine. Upon completion of the piperidine addition, the reaction mixture was refluxed for 2 hours. At the completion of the reaction, the insoluble material contained in the reaction mixture was removed by filtration and benzene thereafter distilled off. The oily residue which remained was taken up in hexane. The 6-chloro-2-(piperidino)pyridine-N-oxide product was recovered by recrystallization from hexane and recovered in a yield of 7.5 grams. The product melted at 38°–41°C. and was found upon analysis to have carbon, hydrogen, chlorine and nitrogen contents of 54.5, 5.9, 19.9 and 12.9 percent, respectively, as compared with the theoretical contents of 56.8, 6.1, 16.7 and 13.2 percent, respectively, calculated for the above named compound.

Example IV:
6-Chloro-2-(1-(2-ethylpiperidino))pyridine-N-oxide

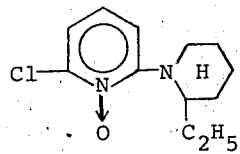

A solution was prepared by dissolving 10.0 grams (0.061 mole) of 2,6-dichloropyridine-N-oxide in 50 milliliters of dimethylsulfoxide. To this solution was slowly added 13.8 grams (0.122 mole) of 2-ethylpiperidine. The mixture was heated to a temperature of ~143°C. and maintained at this temperature for about 2 hours. The reaction mixture was poured into water and thoroughly extracted with methylene chloride. The methylene chloride was removed and the dark syrupy residue which remained was extracted with 500 milliliters of boiling hexane. The oily crude 6-chloro-2-(1-(2-ethylpiperidino))pyridine-N-oxide product was purified by two recrystallizations from hexane and recovered in a yield of 6 grams of a dark oil. Upon analysis, the product was found to have carbon, hydrogen, nitrogen and chlorine contents of 60.5, 6.9, 12.0 and 17.1 percent, respectively, as compared with the theoretical contents of 59.9, 7.1, 14.7 and 15.4 percent, respectively, calculated for the above named structure.

Following the above teachings and reacting the appropriate N-heterocyclic amine with the appropriate dichloro- or dibromopyridine-N-oxide, the following compounds are prepared.

6-Bromo-2-(1-piperidino)pyridine-N-oxide, having a molecular weight of 257.03;

6-Chloro-2-(1-(2-methylpiperidino))pyridine-N-oxide having a molecular weight of 226.58;

6-Bromo-2-(1-(2-n-butylpiperidino))pyridine-N-oxide having a molecular weight of 313.07;

6-Bromo-2-(4-morpholino)pyridine-N-oxide melting at 130°–134°C.;

6-Chloro-2-(1-pyrrolidinyl)pyridine-N-oxide melting at 72°–75°C.;

6-Chloro-2-(1-hexamethylenimino)pyridine-N-oxide melting at 36°–38°C.;

6-Chloro-2-(tetrahydro-1-pyridyl)pyridine-N-oxide a dark brown oil having a molecular weight of 210.58; and 6-Bromo-2-(tetrahydro-1-pyridyl)pyridine-N-oxide having a molecular weight of 255.03.

It has been discovered that the aminohalopyridine-N-oxide compounds which comprise the present invention can be employed for the pre- and post-emergent control of undesirable plant growth. For such uses, the compounds can be employed in an unmodified form or dispersed on a finely divided inert solid and employed as dust. Such mixture can also be dispersed in water with or without the aid of a surface active agent and the resulting aqueous suspension or dispersion employed as a spray. In other procedures, the compounds can be employed as the active constituent in solvent solutions, oil-in-water or water-in-oil emulsions. The augmented compositions are adapted to be formulated as concentrates and subsequently diluted with additional liquid or solid adjuvants to product the ultimate treating compositions.

The exact concentration of the toxicant to be employed in the treating compositions is not critical and may vary considerably provided the required dosage of the effective agent is supplied. The concentration of toxicant in liquid compositions generally is from about 0.0001 to about 50 percent by weight. Concentrations up to about 95 percent by weight are oftentimes conveniently employed, particularly in concentrate compositions. In dusts, the concentrations of the toxicants can be from about 0.1 to 95 percent by weight. For use as a spray, it is often convenient to apply the compounds as wettable powders.

In a representative operation, 6-chloro-2-(isopropylamino)pyridine-N-oxide and 6-chloro-2-(1-piperidino)pyridine-N-oxide were both found to give substantially complete (at least 80 percent) pre-emergent kill and control of pigweeds, wild mustard/charlock and crabgrass, when employed as the sole toxicant, in an aqueous dispersion at a dosage rate equal to 20 pounds per acre.

In another operation, 6-chloro-2-(isobutylamino)-pyridine-N-oxide and 6-chloro-2-(cyclohexylamino)-pyridine-N-oxide were both found to give substantially complete pre-emergent kill and control (at least 85 percent) of pigweeds, wild mustard/charlock, crabgrass, bindweed, barnyard grass, yellow foxtail and wild oats, when employed as the sole toxicant, in an aqueous dispersion at a dosage rate equal to 20 pounds per acre. In other operations, the compound 6-chloro-2-(isobutylamino)pyridine-N-oxide was found to give at least 80 percent pre-emergent kill and control of ragweed, cotton, white winter wheat, corn and Johnson grass in addition to the above listed plants when employed as the sole toxicant in an aqueous dispersion at a dosage rate equal to 10 pounds per acre.

In other operations, 6-chloro-2-(n-butylamino)-pyridine-N-oxide was found to give substantially complete pre-emergent kill and control (at least 80 percent) of wild mustard/charlock, crabgrass and beans, when employed, as the sole toxicant, in an aqueous dispersion at a dosage rate equal to 20 pounds per acre. In other operations, this compound gave at least 90 percent pre-emergent kill and control of pigweeds, barnyard grass and bindweed when employed, as the sole toxicant, in aqueous dispersions at a dosage rate equal to 10 pounds per acre.

In another operation, 6-bromo-2-(isobutylamino)-pyridine-N-oxide was found to give substantially complete pre-emergent kill and control (at least 80 Percent) of pigweeds, wild mustard/charlock, bindweed, barnyard grass and yellow foxtail, when employed, as the sole toxicant, in an aqueous dispersion at a dosage rate of 20 pounds per acre. In other operations, this compound gave 100 percent pre-emergent kill and control of ragweed, soybean, cotton, white winter wheat, crabgrass and Johnson grass, when employed, as the sole toxicant, in an aqueous dispersion at a dosage rate equal to 2 pounds per acre.

In another operation, 6-chloro-2-(isopentylamino)-pyridine-N-oxide and 6-chloro-2-(1-pyrrolidino)pyridine-N-oxide were each found to give good pre-emergent kill and control of wild mustard/charlock and yellow foxtail, when employed, as the sole toxicant, in an aqueous dispersion at a dosage rate equal to 20 pounds per acre.

In other operations, 6-chloro-2-((1,3-dimethylbutyl)amino)pyridine-N-oxide was found to give at least 75 percent pre-emergent kill and control of barnyard grass, bindweed and pigweeds, when employed, as the sole toxicant, in an aqueous dispersion at a dosage rate equal to 10 pounds per acre.

In other representative operations, each of the compounds 6-chloro-2-(4-morpholino)pyridine-N-oxide, 6-chloro-2-(1-(2-ethylpiperidino))pyridine-N-oxide and 6-chloro-2-(1-hexamethylenimino)pyridine-N-oxide were found to give at least 75 percent pre-emergent kill and control of pigweeds, wild mustard/charlock, crabgrass and bindweed, when employed as the sole toxicant, in an aqueous dispersion at a dosage rate equal to 20 pounds per acre.

In another operation, 6-chloro-2-(tetrahydro-1-pyridyl)pyridine-N-oxide was found to give at least 90 percent pre-emergent kill and control of crabgrass and barnyard grass, when employed, as the sole toxicant, in an aqueous dispersion at a dosage rate equal to 20 pounds per acre.

In another operation, each of the compounds 6-chloro-2'-(1-piperidino)pyridine-N-oxide and 6- chloro-2-(1-hexamethylenimino)pyridine-N-oxide were found to give at least 75percent post-emergent kill and control of pigweeds, wild mustard/charlock, crabgrass and yellow foxtail, when employed, as the sole toxicant, in an aqueous dispersion at 4,000 parts per million parts of the ultimate dispersion.

In another operation, each of the compounds 6-chloro-2-(tetrahydro-1-pyridyl)pyridine-N-oxide and 6-chloro-2-(1-(2-ethylpiperidino))pyridine-N-oxide were found to give at least 80 percent post-emergent kill and control of pigweeds, when employed, as the sole toxicant, in an aqueous dispersion at 4,000 parts per million parts of the ultimate dispersion.

In another operation, each of the compounds 6-chloro-2-(n-butylamino)pyridine-N-oxide and 6-bromo-2-isobutylamino)pyridine-N-oxide were found to give at least 80 percent post-emergent kill and control of pigweeds, wild mustard/charlock, bindweed, barnyard grass and yellow foxtail, when employed, as the sole toxicant, in an aqueous dispersion at 4,000 parts per million parts of the ultimate dispersion.

In another operation, 6-chloro-2-(isopropylamino)-pyridine-N-oxide was found to give at least 80 percent post-emergent kill and control of wild mustard/charlock, bindweed and yellow foxtail, when employed, as the sole toxicant, in an aqueous dispersion at 4,000 parts per million parts of the ultimate dispersion.

In other operations, 6-chloro-2-((1,3-dimethylbutyl)amino)pyridine-N-oxide was found to give at least 85 percent post-emergent kill and control of sorghum/milo, when employed, as the sole toxicant, in an aqueous dispersion at 4,000 parts per million parts of the ultimate dispersion.

In another operation, 6-chloro-2-(isobutylamino)-pyridine-N-oxide was found to give at least 80 percent post-emergent kill and control of pigweeds, ragweed, cotton, bindweed, Johnson grass, barnyard grass, beans, sorghum/milo, wild oats, crabgrass and yellow foxtail, when employed, as the sole toxicant, in an aqueous dispersion at 4,000 parts per million parts of the ultimate dispersion.

In other operations, 6-chloro-2-(isopentylamino)-pyridine-N-oxide was found to give at least 80 percent post-emergent kill and control of pigweeds, bindweed and yellow foxtail when employed, as the sole toxicant, in an aqueous dispersion at 4,000 parts per million parts of the ultimate dispersion.

What is claimed is:

1. A compound corresponding to the formula

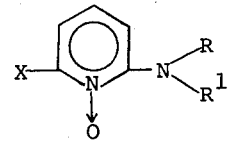

wherein X represents chloro or bromo; R represents hydrogen; R¹ represents a straight or branched chain alkyl of 3 to 6 carbon atoms or cyclohexyl; or R and R¹ taken together with the nitrogen atom represents 1-morpholino, 1-pyrrolidino, 1-piperidino, 1-(2-(loweralkyl)piperidino) (wherein alkyl represents from 1 to 4 carbon atoms), 1-hexamethylenimino or tetrahydro-1-pyridyl.

2. The compound of claim 1 which is 6-chloro-2-(isopropylamino)pyridine-N-oxide.

3. The compound of claim 1 which is 6-chloro-2-(n-butylamino)pyridine-N-oxide.

4. The compound of claim 1 which is 6-chloro-2-(isobutylamino)pyridine-N-oxide.

5. The compound of claim 1 which is 6-bromo-2-(isobutylamino)pyridine-N-oxide.

6. The compound of claim 1 which is 6-chloro-2-(isopentylamino)pyridine-N-oxide.

7. The compound of claim 1 which is 6-chloro-2-((1,3-dimethylbutyl)amino)pyridine-N-oxide.

8. The compound of claim 1 which is 6-chloro-2-(cyclohexylamino)pyridine-N-oxide.

9. The compound of claim 1 which is 6-chloro-2-(1-pyrrolidinyl)pyridine-N-oxide.

10. The compound of claim 1 which is 6-chloro-2-(1-piperidino)pyridine-N-oxide.

11. The compound of claim 1 which is 6-chloro-2-(1-(2-ethylpiperidino))pyridine-N-oxide.

12. The compound of claim 1 which is 6-chloro-2-(1-hexamethylenimino)pyridine-N-oxide.

13. The compound of claim 1 which is 6-chloro-2-(tetrahydro-1pyridyl)pyridine-N-oxide.

14. The compound of claim 1 which is 6chloro-2-(4-morpholino)pyridine-N-oxide.

* * * * *

UNITED STATES PATENT AND TRADEMARK OFFICE
CERTIFICATE OF CORRECTION

PATENT NO. : 3,948,910  
DATED : April 6, 1976  
INVENTOR(S) : Howard Johnston & Alin H. Gulbenk Page 1 of 2

It is certified that error appears in the above-identified patent and that said Letters Patent are hereby corrected as shown below:

First page, last line of OTHER PUBLICATIONS should read --29-36 (1966), C.A., Vol. 66; 10,827;

Column 1, line 56, "6-Chloro-2-(1,3-dimethylpropyl" should read --6-Chloro-2-((1,3-dimethylbutyl)--;

Column 1, line 58, "6-Bromo-2((1,3-dimethylbutyl)" should read --6-Bromo-2-((1,3-dimethylpropyl)--;

Column 1, line 60, "6-chloro" should read --6-Chloro--;

Column 2, line 2, "6-Chloro-2-(1Hexamethylenimino)" should read --6-Chloro-2-(1-Hexamethylenimino)--;

Column 2, line 3, "tetrahydro-lpyridyl)" should read --tetrahydro-1-pyridyl)--;

Column 3, line 41, "9.9 grams" should read --9.0 grams--;

Column 3, line 51, "filtration in the yield" should read --filtration in a yield --;

Column 3, line 52, "melted was" should read --melted at--;

Column 4, line 28, "35 C." should read --35°C.--;

Column 4, line 34, "benzene thereafter" should read --the benzene thereafter--;

Column 5, line 47, "to product the" should read --to produce the--;

UNITED STATES PATENT AND TRADEMARK OFFICE
CERTIFICATE OF CORRECTION

PATENT NO. : 3,948,910
DATED : April 6, 1976
INVENTOR(S) : Howard Johnston & Alin H. Gulbenk It is certified that error appears in the above-identified patent and that said Letters Patent are hereby corrected as shown below:

Page 2 of 2

Colume 6, delete line 68 and substitute --chloro-2-(1-piperidino)pyridine-N-oxide and 6- --;

Column 7, line 7, "In another operation," should read --In other operations,--;

Column 7, line 16, "bromo-2-isobutylamino)" should read --bromo-2-(isobutylamino)--;

Column 8, line 44, "(tetrahydro-1pyridyl)" should read --tetrahydro-1-pyridyl)--;

Column 8, line 45, "which is 6chloro-2-(4-"should read --which is 6-chloro-2-(4- --.

Signed and Sealed this

Thirteenth Day of July 1976

[SEAL]

Attest:

RUTH C. MASON
*Attesting Officer*

C. MARSHALL DANN
*Commissioner of Patents and Trademarks*